US008592224B2

(12) United States Patent
Staab

(10) Patent No.: US 8,592,224 B2
(45) Date of Patent: Nov. 26, 2013

(54) BIOCHIP FOR ARCHIVING AND LABORATORY-MEDICAL ANALYSIS OF BIOLOGICAL SAMPLE MATERIAL, PROCESS FOR ITS PRODUCTION, AND ITS USE IN DIAGNOSTIC METHODS

(75) Inventor: Hans-Jurgen Staab, Starnberg (DE)

(73) Assignee: Bioref GmbH, Mombris (DE)

( * ) Notice: Subject to any disclaimer, the term of this patent is extended or adjusted under 35 U.S.C. 154(b) by 1025 days.

(21) Appl. No.: 11/984,611

(22) Filed: Nov. 20, 2007

(65) Prior Publication Data

US 2008/0138823 A1   Jun. 12, 2008

Related U.S. Application Data

(62) Division of application No. 10/257,661, filed as application No. PCT/EP01/02851 on Mar. 14, 2001, now abandoned.

(30) Foreign Application Priority Data

Apr. 27, 2000 (DE) .................................. 100 20 704

(51) Int. Cl.
*G01N 33/543* (2006.01)
(52) U.S. Cl.
USPC ............ 436/518; 435/7.23; 435/973; 436/64; 436/164; 436/172; 436/501; 436/524; 436/805; 436/809; 436/813; 977/904; 977/918
(58) Field of Classification Search
None
See application file for complete search history.

(56) References Cited

U.S. PATENT DOCUMENTS

| | | | |
|---|---|---|---|
| 4,959,308 A | | 9/1990 | Ogden |
| 5,741,462 A | * | 4/1998 | Nova et al. ...................... 506/37 |
| 5,972,626 A | | 10/1999 | Doxsey |
| 6,066,448 A | * | 5/2000 | Wohlstadter et al. ............. 435/6 |
| 6,087,102 A | * | 7/2000 | Chenchik et al. ................. 435/6 |
| 6,372,185 B1 | * | 4/2002 | Shumate et al. ............... 422/100 |
| 6,406,840 B1 | * | 6/2002 | Li et al. .......................... 435/1.3 |
| 6,475,808 B1 | * | 11/2002 | Wagner et al. .................. 506/18 |
| 6,475,809 B1 | | 11/2002 | Wagner et al. |
| 6,479,301 B1 | | 11/2002 | Balch et al. |
| 6,630,358 B1 | | 10/2003 | Wagner et al. |
| 2001/0014449 A1 | * | 8/2001 | Nerenberg et al. ................ 435/6 |
| 2001/0049111 A1 | * | 12/2001 | Windhab et al. ............... 435/7.1 |

FOREIGN PATENT DOCUMENTS

| | | |
|---|---|---|
| DE | 296 16 373 U | 12/1996 |
| DE | 197 36 470 A1 | 3/1999 |
| DE | 299 06 382 U1 | 11/1999 |
| WO | WO-97/45730 | 12/1997 |

OTHER PUBLICATIONS

Mendoza et al., Biotechniques, vol. 27, No. 4, pp. 778-788 (1999).
Sandoz, Atlas Klinische Hamatologie, HOFFBRAND, Gower Medical Publishing, London (1998), S. 10 and English translation.

(Continued)

*Primary Examiner* — Chris L Chin
(74) *Attorney, Agent, or Firm* — Birch, Stewart, Kolasch & Birch, LLP.

(57) ABSTRACT

A biochip for diagnostic purposes comprises a sample carrier made of a solid matrix, on the surface of said sample carrier is bound the sample material to be analysed which originates from a biological organism.

30 Claims, 4 Drawing Sheets

(56) References Cited

OTHER PUBLICATIONS

S.P.A. Fodor et al., "Light Directed, Spatially Addressable Parallel Chemical SYnthesis", Science 251 (Feb. 1991) pp. 767-773.
C. A. Rowe et al., "An Array Immunosensor for Simultaneous Detection of Clinical Analytes", Analytical Chemistry, vol. 71 (Jan. 15, 1999) pp. 433-439.
J. Cheng et al., "CHIP PCR. II. Investigation of Different PCR Amplification Systems in Microfabricated Silicon-Glass Chips", Nucleic Acids Research, Vo. 24 (1996) pp. 380-385.
M. Eggers et al., "A Microchip for Quantitative Detection of Molecules Utilizing Luminescent and Radioisotope Reporter Groups", Biotechniques 17 (1994) pp. 516-523.
T. Vo-Dinh et al., "DNA Biochip Using a Phototransistor Integrated Circuit", Analytical Chemistry 71 (1999) pp. 358-363.
M. Schena et al., "Auantitative Monotoring of Gene Expression Patterns with a Complementary DNA Microarray", Science 270 (Oct. 20, 1995) pp. 467-470.
L. C. Shriver-Lake, "Antibody Immobilization Using Heterobiofunctional Crosslinkers", Biosensors & Bioelectronics vol. 12, (1997) pp. 1101-1106.

* cited by examiner

FIG. 2
FIG. 2A
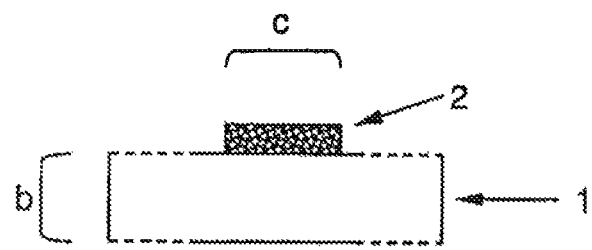
FIG. 2B
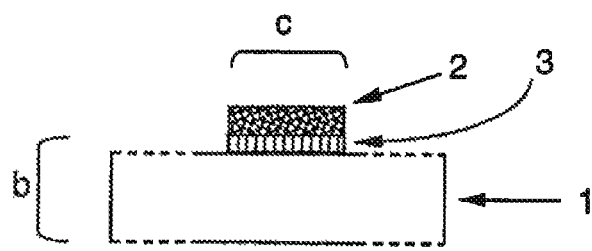
FIG. 2C
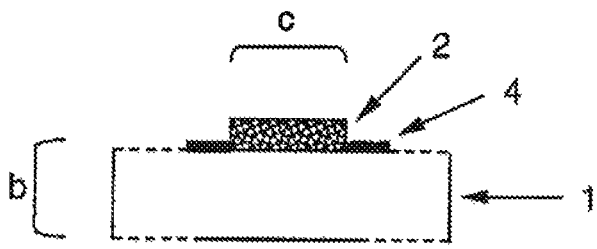
FIG. 2D
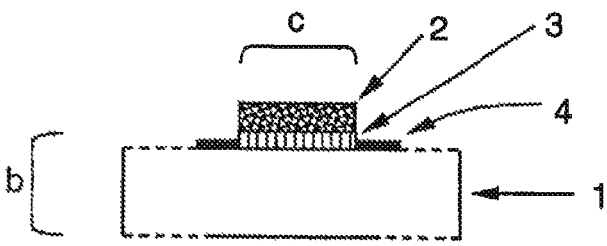

FIG. 3
FIG. 3A
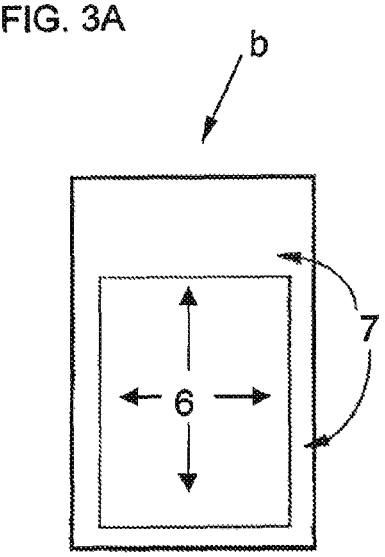
FIG. 3B
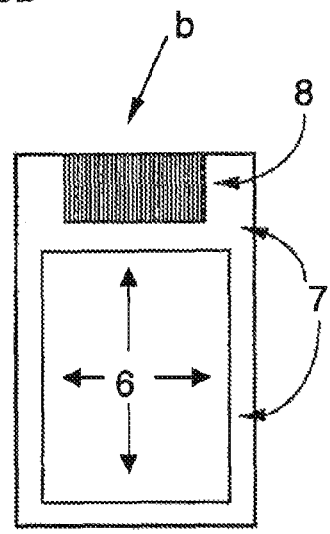
FIG. 3C
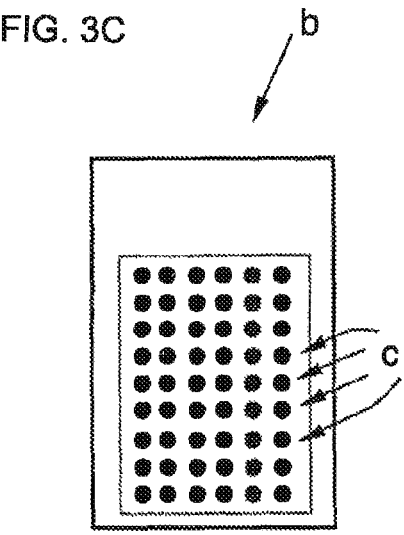
FIG. 3D
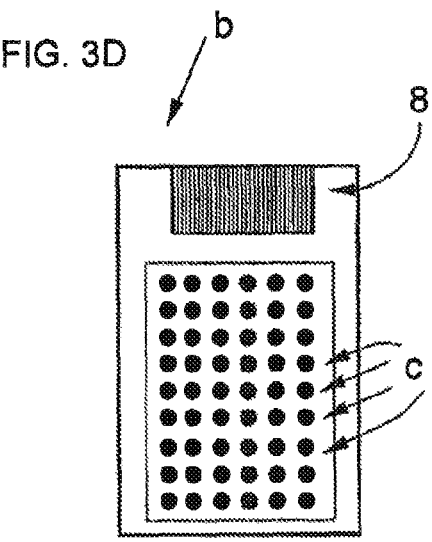

BIOCHIP FOR ARCHIVING AND LABORATORY-MEDICAL ANALYSIS OF BIOLOGICAL SAMPLE MATERIAL, PROCESS FOR ITS PRODUCTION, AND ITS USE IN DIAGNOSTIC METHODS

This application is a Divisional Application of U.S. application Ser. No. 10/257,661, filed on Dec. 24, 2002 now abandoned, which is the national phase under 35 U.S.C. §371 of PCT International Application No. PCT/EP01/02851 which has an International filing date of Mar. 14, 2001, which designated the United States of America.

FIELD OF THE INVENTION

The invention relates to a biochip suitable for diagnostic purposes, which is coated with the biological sample material to be analysed, and which is suitable both for space-saving archiving of sample material and for the laboratory-medical diagnostic analysis thereof. The invention further relates to sample carriers suitable for the production of such biochips, and to processes for the production of the sample carriers or biochips mentioned. The invention further relates to diagnostic methods using the biochips of the present invention, as well as to the use of the biochips of the present invention or of the diagnostic methods in various medicinal areas.

BACKGROUND OF THE INVENTION

Laboratory-medical diagnostics constitutes an important basis for medical treatment. Due to the rising number of available diagnostic marker molecules, the possibilities of laboratory-medical diagnostics are being continuously expanded. Because of the volume of the detection reactions to be carried through, their great urgency, as well as for economical reasons, automated analysis methods, which are able to cope with a large number of different analyses within a short time, are employed with preference.

The raw material for the laboratory-medical analysis of a patient's state of health is typically a body fluid such as whole blood, plasma, serum, urine, ascites, amniotic fluid, saliva, liquor, etc., or tissue samples of different organs. The treating physician collects the sample from the patient, possibly subjects the same to a specific treatment, e.g. centrifugation, and then transfers the patient sample into a test tube, in which the sample is sent out or stored until the analysis is performed.

Depending on the parameter to be analysed, i.e. the components (analytes) to be analysed, the sample may either be stored at room temperature, or it has to be cooled, or stored in frozen condition. In the case of long-term storage, i.e. if the storage is for a period of several weeks, months or years, the patient samples must be frozen at −20° C. or at lower temperatures in order to prevent degradation of the analytes. The main cause for the degradation occurring at room temperature is the enzyme activities inherent in the liquid sample material.

Typical sample volumes for long-term storage amount to at least 500 µl. If, after a first analysis, further analytical determinations are to be made at a later point in time, or at various later points in time, several 500 µl samples have to be prepared starting from the original collection of blood, and stored, or stored in deep-frozen condition. These samples take up a relatively large space, which renders storage over a prolonged period of time relatively expensive. For this reason, long-term storage of patient samples is as a rule not applied. This, however, means that one has to forgo the possibility of at a later time falling back upon a sample collected earlier. In many cases, this is desirable or even necessary, namely when it is important to compare a patient's current condition, in terms of certain diagnostic parameters, with an earlier states of the same patient. As the case may be, it may be useful to record several earlier conditions in a patient at various points in time in order to perform a trend analysis for the relevant parameter. Such comparisons are, however, not possible where the relevant diagnostic test(s) were not, or could not be, made at the earlier point(s) in time in question and the original sample(s) was/were not stored.

For analysis of a patient's state of health, methods of the most different kind are currently utilized in laboratory medicine. Among these are first of all the activity determination of enzymes, special colouring reactions, immunochemical methods, cytological methods, and molecular-biological methods. In recent years, immunochemical methods have gained significance above all, and they have replaced many conventional methods. Molecular-biological methods are also increasingly making an entrance in routine diagnostics.

The currently utilized immunochemical analysis systems are based on antigen-antibody reactions, which mostly take place in a volume of ca. 10-500 µl. Here, the patient sample (body fluid, etc.), which contains the analyte to be detected, in this case an antigen, is incubated together with an antibody which is specific for this parameter and recognizes and binds to only this analyte. The product of this antigen-antibody reaction is a complex containing antibody-bound antigens. The higher the antigen concentration in a patient sample, the higher the concentration of antigen-antibody complexes formed. In current test systems, these antigen-antibody reactions take place either freely in solution (detection by turbidimetry or nephelometry), or they are performed on antigen-specific surfaces (e.g. RIA, ELISA). When the antigen-antibody reaction has taken place, in the first case the antigen-antibody complexes are in solution, in the second case they are bound to a solid phase, mostly a plastics surface. The detection and quantification of antigen-antibody complexes is performed in the case of turbidimetry or nephelometry by measuring the turbidity, in the case of RIA (radioimmunoassay) by radio-isotope-marked antibodies in conjunction with radiometric detection, in the case of ELISA (enzyme-linked immunosorbent assay) and LIA with enzyme-marked antibodies in conjunction with the detection of enzyme-catalysed colour-reactions. By means of these test systems, analyte and antigen concentrations can be detected in the range of up to 1 pg/ml (protein).

The miniaturization and automation of the above-mentioned analysis systems, which are established in laboratory technology, are currently intensively researched. Thus, in recent years, various miniaturized, solid-phase-linked test systems have been developed, which because of their small size are called "biochips" in analogy to computer chips. The size of such biochips is typically between 0.25 and 9 cm². Biochips described in the literature consist of a solid matrix of glass (S. P. A. Fodor et al.: Light-directed, spatially addressable parallel chemical synthesis; Science 251 (February 1991), p. 767-773); C. A. Rowe et al.: An array immunosensor for simultaneous detection of clinical analytes; Analytical Chemistry Vol. 71 (Jan. 15, 1999) p. 433-439; L. G. Mendoza et al.: High-throughput microarray-based enzyme-linked immunosorbent assay (ELISA); BioTechniques 27 (October 1999), p. 778-788), nylon or nitrocellulose membrane, silicone (J. Cheng et al.: Chip PCR. Nucleic Acids Research Vol. 24 (1996) p. 380-385), or silicon. Via different linker molecules, it is possible to covalently couple biomolecules, e.g. DNA, peptides or proteins, to those matrices. On a surface of 3.6 cm² can be applied up to 10000 different biomolecules, which requires micrometer-accurate addressing of the biomolecules to special areas of the matrix which are separated from each other. This can be achieved, for example, by photolithographically controlled synthesis of the biomolecules (S. P. A. Fodor et al.: Light-directed, spatially addressable parallel chemical synthesis; Science 251 (February 1991), p. 767-773), or by spotting-on of the biomolecules by means of precision-mechanical, microprocessor-controlled programmable pipetting robots (L. G. Mendoza et al.: High-throughput microarray-based enzyme-linked immunosorbent assay (ELISA); BioTechniques 27 (October 1999), p. 778-788; M. Eggers et al.: A microchip for quantitative detection of molecules utilizing luminescent and radioisotope reporter groups; BioTechniques 17 (1994) p. 516-523).

By means of the solid phase-bound biomolecules, the analytes to be analysed which are contained in the patient samples, can subsequently be bound and detected with suitable detection systems.

As detections systems of high sensitivity, there are employed, for instance, charge-coupled-device (CCD) cameras (L. G. Mendoza et al., M. Eggers et al.; loc cit.), phototransistors (T. Vo-Dinh et al.: DNA biochip using a phototransistor integrated circuit; Analytical Chemistry 71 (1999) p. 358-363), and fluorescence detectors (S. P. A. Fodor et al.; loc cit.).

The above-described biochips are currently being used exclusively for research purposes, e.g. for DNA sequencing, gene expression analysis, gene mutation analysis and protein-binding studies, i.e. antibody-binding studies.

In gene expression analysis (M. Schena et al.: Quantitative monitoring of gene expression patterns with a complementary DNA microarray; Science 270 (20 Oct. 1995) p. 467-470), DNA sequences which are complementary to certain genes are spotted on with the aid of a pipetting robot onto the matrix of a chip blank, with every single spot representing a certain gene. Subsequently, mRNA is isolated from the tissue sample to be analysed, marked with a fluorescent dye and applied on the entire biochip. Then, the binding of marked mRNA molecules to certain sites of the biochip can be detected. When the analysis has been carried through, the biochip is discarded as it is contaminated with the mRNA sample.

In a similar way, biochips can be utilized for DNA sequence analysis and for gene mutation analysis.

For immunochemical analysis of the sample material, Mendoza et al. (loc cit.) have described a prototype of a miniaturized test system. The authors used a special glass slide with 96 depressions ("wells"), each depression being printed, using a pipetting robot and a capillary printing method, with a pattern of spots consisting of 144 different antigens. After incubation with antibody-containing solution, those spots where antigen-antibody complexes have been formed can be detected by means of a CCD camera.

Hence, the biochips known from the prior art are restricted to such embodiments where specific, selected, or especially synthesized molecules are applied and bound to a solid matrix in a defined, miniaturized arrangement. These molecules serve to detect the presence of certain analytes in a heterogeneous mixture, e.g. the patient sample. This means that these biochips are test-specific, i.e. they allow only for those detection reactions which are pre-determined by the detection molecules present on the chip.

This approach has several disadvantages in respect of laboratory diagnostic applications. It is true that with this approach it is possible to perform a large number of different determinations at the same time; for a concrete problem, however, mostly only a limited number of parameters, i.e. analytes, is relevant. This means that the plurality of the detection molecules present on such a chip remains unused or is of no interest. In addition, one has to take into account that after incubation with the patient sample such a biochip can as a rule not be used for further analyses. For these reasons, the use of biochips of the type described is little suited for routine detection methods in laboratory medicine, and they can not be utilized in a cost-effective manner.

Furthermore, in the hitherto known biochips, new patient sample material is need for each further analysis to be carried out. The consequence is that the patient possibly has to appear several times for taking blood samples, which involves a certain effort both on the part of the physician and on that of the patient. If a certain examination is to be repeated at a later point using the sample material already collected, an intermediate storage of the sample material in liquid or; frozen condition will be necessary, which involves the above described drawbacks.

As a consequence of the progress in development, novel detection reactions are constantly being made accessible. To render the biochips known from the prior art usable for such newly developed detection reactions, the biochips would constantly have to be brought up to date, which involves high expenditure and, in addition, is only possible with a certain delay in time.

Often, at the time a new detection method becomes available, the original sample material of a certain patient is no longer available, so that it is mostly not possible to examine an alteration in time of the laboratory-medical parameter that is of interest, since the longer-term storage of patient sample material is problematic. The biochips known form the prior art cannot contribute to a solution of this problem.

SUMMARY OF THE INVENTION

The task underlying the invention was therefore to provide a miniaturized analysis system in the form of a biochip for diagnostic purposes, which analysis system was to enable repeated execution of analytical detection methods, even at longer intervals of time, on the same patient sample material. Furthermore, the biochip was to enable the space-saving storage and archiving of the sample material for a prolonged period of time.

In addition, the task underlying the invention was to provide a method enabling the automated implementation of detection reactions with a biochip complying with the aforementioned prerequisites. The method should be highly flexible, i.e. it should be easily adaptable to other, originally not intended detection reactions. In addition, the process was to enable repeated examination of the same sample material at intervals of time.

Surprisingly it was found that the aforementioned problems could be solved by a biochip according to claim 1 and by a diagnostic detection process according to claim 17. The subclaims refer to further embodiments of the invention which likewise solve the above-mentioned problem.

According to claim 1, the biochip according to the invention comprises a sample carrier made of a solid matrix, to the surface of which is linked the sample material to be analysed, which sample material originates from a biological organism. Thus, the sample material to be analysed is linked to a solid phase.

In contrast to the biochips known from the state of the art, in the present case no specifically selected or synthesized molecules are bound to the chip surface, but, instead, the sample material itself, e.g. a body fluid constituting a heterogeneous mixture of different biomolecules. Hence, the biochip according to the present invention represents a patient-specific or patient sample-specific chip, whereas the hitherto known biochips are test-specific, i.e. detection-specific biochips.

The binding of the sample material can be directly to the surface of the sample carrier matrix. Preferably, the matrix or surface of the sample carrier is pre-treated by chemical or physical methods in order to improve the binding capacity of the surface for the sample material. Methods suitable for this purpose, e.g. etching or roughening, are known to those skilled in the art.

BRIEF DESCRIPTION OF THE DRAWINGS

The present invention will become more fully understood from the detailed description given hereinbelow and the accompanying drawings. The drawings are not to scale, and are given by way of illustration only. Accordingly, the drawings should not be construed as limiting the present invention.

FIG. 2 A shows a section through a biochip in the region of a micro-area (c), with (b) again designating the sample carrier consisting of a solid matrix (1). As can be seen therefrom, the biological sample material (2) is bound to the surface of the sample carrier only in the region of the micro-area (c). The adjacent regions of the sample carrier surface are free of sample material.

FIG. 2 B likewise shows a section through a biochip in the region of a micro-area (c), similarly to FIG. 2 A, however, with the sample material (2) being bound to the matrix (1) of the sample carrier (b) via a linker layer (3). The linker layer is present only in the region of each micro-area; the adjacent regions are free of linker molecules.

FIG. 2 C likewise shows a section through a biochip in the region of a micro-area (c), similarly to FIG. 2 A. Here, however, the border regions (4) surrounding each micro-area are provided with hydrophobic properties, or they are non-wettable, so that in these border regions no sample material (2) can be bound.

FIG. 2 D shows an embodiment in a representation as in FIG. 2 A wherein the measures shown in FIGS. 2 B and 2 C are combined with each other. The sample material (2) is linked via a linker layer (3), which is situated in the region of the micro-area (c), to the matrix of the sample carrier. In addition, the border regions (4), which surround each micro-area, have been provided with hydrophobic properties or made non-wettable.

FIG. 2 E shows a further embodiment in a representation as in FIG. 2 A. Here, a micro-area (c) is shown which is configured in the form of a depression (5) in which the sample material (2) is bound to the matrix (1) of the sample carrier (b).

FIG. 2 F shows a variant of the embodiment depicted in FIG. 2 E, in which a micro-area (c) is shown which is configured in the form of a depression (5) the bottom of which is coated with a linker layer (3) by means of which the sample material (2) is bound to the matrix (1) of the sample carrier (b).

FIG. 2 G shows a variant of the embodiment depicted in FIG. 2 E, with the depression (5) of the micro-area (c) being configured in the form of a rounded trough.

FIG. 2 H shows a variant of the embodiment depicted in FIG. 2 F, with the depression (5) of the micro-area (c) being configured in the form of a rounded trough.

FIG. 3 shows, by way of example, some embodiments of the biochip or sample carrier according to the invention, in plan view.

FIG. 3 A shows the basic shape of a biochip or sample carrier (b) according to the invention, with the surface area to be coated with the sample material being designated as (6). The regions outside the surface area (6), especially the border regions, may be rendered hydrophobic or non-wettable.

FIG. 3 B shows a variant of the sample carrier (b) depicted in FIG. 3 A, which, in addition (8), is equipped with a bar code, magnetic strip or another storage medium.

FIG. 3 C shows a sample carrier (b) or biochip in plan view, with the arrangement of the mentioned micro-areas (c) being represented by way of example. As in FIGS. 3A and B, here, too, the border regions may be rendered hydrophobic or non-wettable.

FIG. 3 D finally shows a variant of the embodiment depicted in FIG. 3 C, in which—as in FIG. 3 B—additionally a means for data storage is provided, e.g. a bar code, magnetic strip or another storage medium.

DETAILED DESCRIPTION OF THE INVENTION

Figure 1:
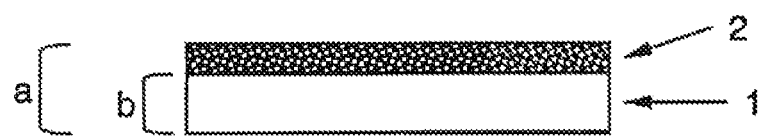
FIG. 1A shows a section through a biochip (a) according to the invention which consists of a sample carrier (b) and the sample material (2) bound to the surface thereof. The sample carrier (b) substantially consists of a solid matrix (1).
FIG. 1B shows, in section, an embodiment of the biochip (a) according to the present invention, wherein the sample carrier (b) comprises a solid matrix (1) and additionally a linker layer (3) located thereon. The sample material (2) is linked to the matrix via the linker layer (3) of the sample carrier.
Figure 1:
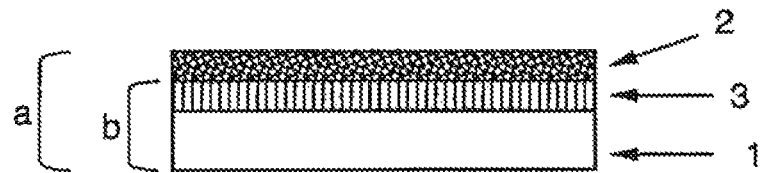
Figure 2E:
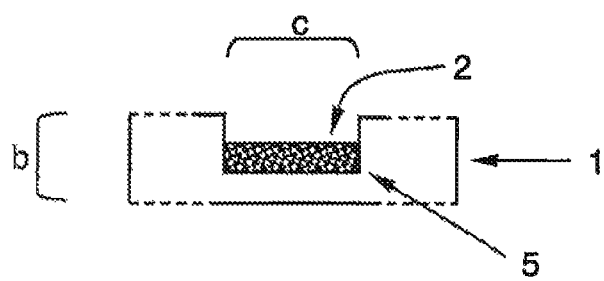
FIG. 2 shows sectional representations of different embodiments of the biochip according to the present invention, which embodiments comprise the afore-mentioned micro-areas (c). In each of the FIGS. 2 A to H there is depicted a region of a biochip in which such a micro-area is situated.
Figure 2F:
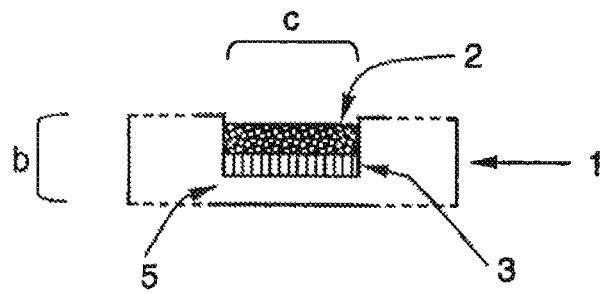
Figure 2G:
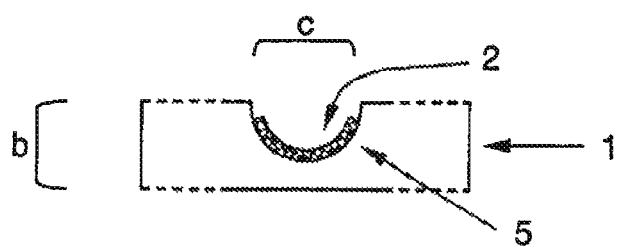
Figure 2H:
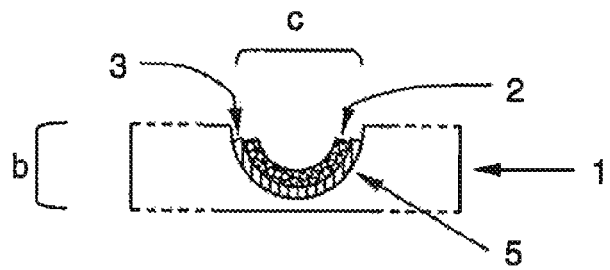

The general structure of the biochips according to the present invention can be seen from FIG. 1A, which represents a biochip (a) in section comprising a sample carrier (b) and a sample material (2) bound thereto. The sample carrier substantially consists of a solid matrix (1).

The binding of the sample material may optionally also be carried out by means of a layer of linker molecules (linker layer) applied to the surface of the sample carrier.

The schematic structure of such a biochip (a) can be seen in FIG. 1B, which represents a sample carrier (b) in section consisting of a solid matrix (1) and a linker layer (3) located thereon; the sample material (2) is bound on the surface of the sample carrier via the linker layer.

With the biochips of the present invention, the diagnostic detection reaction is principally carried through in such a manner that the molecules suitable for the detection are applied to very small areas of the biochip, which is coated with the sample material, as will be described in detail below. In this way, it is possible to treat different areas of the surface of the biochip with different diagnostic detection reagents either simultaneously or successively.

Since in the biochips of the invention the sample material to be analysed—and not the molecules used for detection—is bound to the surface of the sample carrier forming the matrix of the biochip, the use and field of application of such a chip is not restricted to certain, selected diagnostic molecules owing to the manner of its manufacture. Rather, the selection of the useful or required diagnostic detection reagents is made only when the detection method is being applied, thereby achieving a high flexibility of application.

In the biochips according to the invention, the sample material to be analysed is bound to the surface of the sample carrier. The sample material is present in dried condition and is therefore stable in storage even at room temperature. Since the biochips of the invention are miniaturized systems, in this way a space-saving and economical storage and archiving of patient sample material is made possible. In this manner, a large number of the patient-specific biochips according to the present invention can be stored in a small space and is available for performing multiple analytical detection reactions.

The archivability of the biochips, in conjunction with the possibility of performing several detection reactions on various sites of the chip surface independently from each other, enables the examination of a specific diagnostic marker in a specific patient, or in a specific sample of a patient, at different intervals of time. It is especially advantageous that such diagnostic examinations are possible at a later point in time even in such cases where they have not been planned originally, i.e. at the time of collecting the sample. This applies especially to such detection reactions which have been developed at a later point in time after the collection.

Preferably, each individual specimen of a biochip according to this invention contains sample material which has in each case been collected from a certain, individual biological organism, e.g. sample material originating from a certain patient. Apart from humans, further biological organisms from which suitable sample material may be obtained are animals, plants, fungi and microorganisms.

Preferably used as the sample material linked to the surface of the biochip are body fluids such as, for instance, whole blood, plasma, serum, urine, ascites, amniotic fluid, saliva, liquor, lavage material from body cavities or bronchoalveolar lavage. Likewise, tissue samples or organ samples, or components, cells, fractions, cell-disintegration material, concentrates or extracts from the mentioned fluids or from tissue or organ samples may be used. In certain cases it may be appropriate to pretreat the sample in such a manner that the analytes which are of interest—if they are contained in the sample—are concentrated therein. For a serum analysis, for example, the solid components of the blood sample are separated by centrifugation; subsequently the serum obtained in this manner can be applied and bound to the surface of the sample carrier.

In a particularly advantageous embodiment, the surface of the sample carrier according to this invention, which surface is loaded with sample material, is partitioned into microareas. These are very small surface areas which are arranged close together, but are separated from each other. Usually, the surface is subdivided into a plurality of such micro-areas, preferably at least 100 micro-areas per $cm^2$. For certain application purposes, a smaller number of micro-areas per unit area may be sufficient, e.g. 10 to 100 micro-areas per $cm^2$. The micro-areas may preferably be configured as depressions or separated from each other by hydrophobic or non-wettable border regions. By providing the sample carrier with hydrophobic or non-wettable border regions it is possible to prevent the linkage of sample material in these regions, so that these border regions, which are located between the individual border regions, are free from sample material. The configuration of the micro-areas will be illustrated further below, by way of example, in FIGS. 2 and 3.

By partitioning the chip surface into micro-areas, the implementation of analytical detection reactions is improved since this measure facilitates the detection and treatment of single sites by a pipetting robot. Especially if the micro-areas are applied in the form of a regular grid or screen, it is possible to identify and address individual micro-areas by means of their coordinates. Thereby, the selective application of detection reagents to individual sites of the biochip using a pipetting robot is simplified. At the same time, the partitioning of the chip surface coated with the sample material increases the detection reliability, respectively prevents the risk of unwanted reactions or contaminations, as the individual micro-areas are separated from each other by border regions or are present in the form of depressions.

The sample carrier of the biochip according to the present invention, to whose surface the sample material is bound, substantially consists of a solid matrix. Suitable base materials for the matrix of the sample carrier are, for instance, silicone, plastics (e.g. polyvinyl chloride, polyester, polyurethane, polystyrene, polypropylene, polyethylene, polyethylene terephthalate, polyamide, nitrocellulose) or glass, but other solid materials may be used as well. Transparent solid materials are used with preference. However, when selecting the matrix material, on must take care that it be suitable for durably binding the intended sample material. The sample carrier may also be a laminate of at least two different matrix materials, with preferably one of the two layers forming a rigid carrier layer and the other layer serving as the surface for binding the sample material.

As already discussed above, it is of particular advantage if the surface of the sample carrier, to which the sample material is to be linked, is subdivided into microareas.

The outer dimensions of the biochips according to the present invention are selected such that the requirement of miniaturisation is fulfilled. The surface of such a biochip, or of a sample carrier for production of such a biochip, should be at most 10 $cm^2$, preferably at most 4 $cm^2$, and especially preferred at most 1 $cm^2$.

With preference, the sample carrier, respectively the biochip, is configured as a flat-shaped body, with particular preference having a square or rectangular outline. But other geometric shapes may be suitable too, e.g. round or circular sample carriers or biochips.

The thickness of the flat-shaped sample carrier is preferably less than 3 mm, especially preferred less than 1 mm. In the individual case, the outer dimensions of the biochip are selected such that they are compatible with already available pipetting robots or analysis automatons and enable the use of the biochips according to the invention in such appliances.

To produce a biochip of the present invention, the surface of a sample carrier is coated with the biological sample material, and this material is bound to the surface of the sample carrier; this bond may be covalent or non-covalent. In order to improve the capability of binding sample material, respectively of binding biomolecules, when using certain matrix materials as sample carriers, it may be useful to subject these materials, respectively the surface of the sample carrier, to a pre-treatment using chemical or physical methods (e.g. etching), thereby increasing the binding capacity. Furthermore, by chemical or physical pre-treatment, the surface of the sample carrier can be enlarged, which leads to an increase in the binding capacity. Methods suitable for this purpose are known to those skilled in the art.

According to a preferred embodiment of the invention, the surface of the sample carrier may be provided with a linker layer prior to application of the sample material in order to improve the binding of the sample material, respectively of the analytes (e.g. biomolecules or cells) contained therein, to the surface of the sample carrier, or to bring about a selective or preferred binding of certain analytes or groups or classes of analytes. In this way it is possible to achieve a concentration or pre-selection of certain analytes or groups of analytes. In this connection, linkers are understood to mean such chemical compounds which on the one hand are capable of entering into a firm bond with the surface of the sample carrier, i.e. with its matrix material, and on the other hand are capable of binding biological sample material, or binding the latter selectively or in a preferred manner.

Preferably, the surface of the sample carrier may be provided with a layer of linker molecules which enable the selective binding or concentration of certain groups of biological macromolecules, preferably of proteins, peptides, glycoproteins, sugars, lipids, nucleic acids, or the binding or concentration of cells or certain cell types or cell populations.

It may further be advantageous to coat different area portions of the surface of a sample carrier with different types of linker molecules. In this way it is possible to carry through a pre-selection and spatial separation of the analytes (e.g. different classes of biological macromolecules) present, for example, in a patient sample.

As linker molecules may be used, for example (L. C. Shriver-Lake; Antibody immobilization using heterobifunctional crosslinkers; Biosensors & Bioelectronics Vol. 12 (1997), p. 1101-1106): N-succinimidyl-4-maleimidobutyrate (GMBS; for binding of amino groups), 4-(N-maleimidomethyl)-cyclo-hexane-1-carboxylhydrazide-HCl (M2C2H; for binding of residual sugar), or antibodies with known binding specificities for binding the most different macromolecules or cells or types of cells.

As already mentioned, it is of advantage if the surface of the sample carrier or biochip is partitioned into micro-areas. Apart from the already described methods, this partitioning may also be achieved by a discontinuously configured linker layer. In this case, micro-areas of linker-containing surface areas, and linker-free zones located therebetween are formed, with preferably at least 100 micro-areas being present per $cm^2$.

The manufacture of a sample carrier the surface of which is suitable for binding sample material thereto and is preferably subdivided into micro-areas, can be accomplished in various ways. For making surface pieces having the dimensions suitable for biochips, the sheet-like matrix raw material (glass, plastics, etc.), which is usually present in large size, is separated in a corresponding manner using known mechanical methods, thereby obtaining sample carriers. As an alternative, the corresponding matrix raw material may be liquefied and subsequently cast into appropriate moulds, e.g. by injection moulding, to produce sample carriers.

The micro-areas mentioned, respectively the intermediate border regions, can be produced, for example, by employing physical methods such as engraving, punching, embossing or printing, or by chemical methods such as etching or applying hydrophobic layers. It is furthermore possible to apply linker layers in the form of micro-areas to the surface of the sample carriers with the aid of a pipetting robot. Also, various known printing methods may be adapted to enable the production of the micro-areas of the present invention. Finally, the aforementioned methods can also be utilized in combination. Furthermore, it is possible to carry through the subdivision into micro-areas already in the matrix raw material, which is present in sheet-like form, said matrix raw material subsequently being separated into individual sample carriers in the manner described.

The biochips according to the present invention are especially suitable for archiving and multiple diagnostic analysis of sample material from one particular patient per biochip ("patient-specific" biochip). To facilitate, or to make possible, the archiving of such chips and their automatic processing and evaluation in analysis automatons it is proposed according to a further embodiment of the invention that the biochip or a corresponding sample carrier be provided with means which enable the identification of the biochips, or the storage of patient-related data, or the storage of analysis data.

This can preferably be done by means of a machine-readable bar code, a machine-readable magnetic strip, a digital storage element or another computer-readable storage medium. Especially where large numbers of patient-related biochips have to be archived or processed, the above described embodiment is of advantage.

The presence of a means for data storage on the biochips makes it possible, for example, for the physician or the laboratory physician collecting the sample and possibly applying the sample material to the sample carrier, to store, for example, patient-related data, or data relating to the collection of the sample on the biochip. Furthermore, it is thereby also possible to store analysis results or their evaluation, so that information on analyses which have already been performed earlier can also be stored.

The invention further comprises diagnostic detection methods comprising process steps for manufacturing a biochip using sample material, as well as comprising process steps for carrying out diagnostic detection reactions and for the evaluation thereof.

Initially, body fluids, tissue samples or the like are obtained from a patient or from another organism, and, if required, subjected to pre-treatment (e.g. centrifugation, concentration, etc.). If required, the sample material is suspended or dissolved in a suitable buffer or solvent. To produce a biochip, this sample material, preferably in liquid form, is applied to the surface of a sample carrier according to the present invention, e.g. by means of a pipette or by dipping. After a short incubation time of a few minutes, e.g. 1 to 10 min., any excess sample material is removed (e.g. by suction). Subsequently, drying takes place, preferably at slightly elevated temperatures (30-60° C.), thereby causing the sample material, respectively the analytes (e.g. biomolecules) contained therein, to be linked to the surface of the sample carrier, or, as the case may be, to the linker layer. The aforementioned process steps may be carried out by the physician collecting the sample material, or by auxiliary medical staff.

The patient-specific or sample-specific biochips thus obtained can subsequently be stored at room temperature under dry conditions, and are ready for immediate or later analysis.

To perform analytical detection reactions on such a biochip coated with sample material, in the subsequent steps the desired detection reagents are applied to individual sites or to individual micro-areas of the said biochip, preferably using a pipetting robot. Suitable as detection reagents are, for example, antibodies, antigens, sequence-specific antibodies, lectins, DNA probes, low-molecular ligands, hormones, biomolecule-binding dyes or other specifically binding molecules.

The mentioned sites or micro-areas of the biochip are incubated, for a certain time and at a certain temperature, with the selected detection reagents at certain concentrations, the experiment parameters in each case being dependent on the kind of detection reagents used and on the respective sample material. Those skilled in the art will normally be familiar with the selection of suitable experimental parameters.

When the end of the determined incubation time has been reached, the liquid detection reagent is removed by suction, using a pipetting robot. Subsequently, in a next step, likewise utilizing a pipetting robot, wash solvents and, if required, further detection reagents are applied in sequential order to the sites or micro-areas to be analysed and thereafter sucked off. The wash solutions and the detection reagents to be used in addition, e.g. fluorescence-marked antibodies, as well as the suitable reaction conditions are in principle known to those skilled in the art.

Finally, those sites or micro-areas where a positive detection reaction has taken place are identified by a suitable detector. Registration of these measurement signals is preferably accomplished with the aid of CCD cameras, phototransistors, or radioactivity, luminescence or fluorescence detectors, the selection of the detection method being dependent on the kinds of detection reagents used. The primary measurement data supplied by the detectors can then be subjected to a computer-aided evaluation.

Positive detection reactions are in principle brought about by a specific interaction or linkage between the analytes (e.g. certain antigens in the patient sample) and the detection reagent used, e.g. by forming antigen-antibody complexes. These are made detectable by further reaction steps or reagents, which are known to those skilled in the art.

It is particularly advantageous if a larger number of the biochips according to the invention, e.g. from different patients, are analysed simultaneously or parallelly in the manner described, i.e. if the detection reactions and the detection are performed simultaneously or parallelly on a plurality of biochips.

It is furthermore of advantage if the biochip or biochips is/are treated parallelly (at the same time) or sequentially one after the other, with different detection reagents possessing different detection specificities, said detection reagents in each case being applied to sites or micro-areas which have not previously been examined. In this way, it is possible to test, within an extremely short period of time, on the presence or absence of certain diagnostic marker molecules in a plurality of patient-specific biochips. To prevent a certain site or micro-area of a biochip from being used several times for a detection reaction, it may be provided that the position of the already "used-up" sites or areas be registered and stored on the storage medium of the biochip.

Furthermore, it is also possible to analyse different sites or micro-areas of the same biochip with the same detection reagent, possibly at different concentrations. In this way, the detection reliability can be increased by multiple or, respectively, parallel measurements.

After the detection reaction and the detection have been carried through, the biochips can be returned for archiving and storing. They are then available for further detection reactions. This means that the same biochip which is coated with the sample material of a certain patient can be subjected twice or several times successively to an analysis, involving detection reaction, detection and evaluation, in accordance with the above-described steps, with said biochip being stored or archived during the time between the successive analyses. In the successive analyses, different micro-areas of the biochip are treated with different detection reagents.

Due to the possibility of performing a plurality of diagnostic detection reactions—even at longer intervals of time—on a single biochip, the quantity of sample material needed is considerably reduced, i.e. on the basis of a relatively small quantity of the initial sample (e.g. 0.5 ml), it is possible to produce biochips enabling a large number of detection reactions over a prolonged period of time.

The biochips according to the present invention together with the raw material bound thereon are, at room temperature, storable for a several years, at least for a period of 5 years, and during this storage time can be used repeatedly for carrying out the detection reactions described. The biochips of the present invention are therefore advantageous in all those cases where it is important to store or archive sample material from patients affording the possibility of performing diagnostic detection reactions.

In special cases, where the stability of certain analytes in the sample material appears critical, the biochips may also be stored at lower temperatures, e.g. at 0° C. to 15° C. or at even lower temperatures, e.g. below 0° C. In principle, it is to be expected that after a prolonged storage, or a storage lasting several years, of the biochips in dried condition, an extensive inactivation of the potentially degrading enzymes, such as nucleases or proteases, has taken place.

The biochips of the invention can expediently be stored or archived in a closable case or box which has guide rails on its inner side walls along which the biochips can be inserted into the case and by means of which they are locked therein. By providing a plurality of such guide rails, it is possible to accommodate more than 100 biochips in a space-saving manner in a single case. A large number of those cases can in turn be integrated as an immovable or movable component in a drawer system or cupboard system.

Due to their storability and to the possibility of performing a large number of independent detection reactions, the biochips according to the present invention, respectively the diagnostic detection methods according to the present invention, are suitable for a plurality of practical applications. In the following, some possibilities of application will be described.

The biochips according to the present invention can be used in the field of tumour diagnostics to monitor, for example, the appearance of certain tumour markers in the serum or in tissue samples. These tumour markers are formed by tumours and secreted in body fluids of a sick person, or they are formed by the organism as a result of its reaction to the tumour. By contrast, these marker molecules are absent in the serum or other body fluids of healthy persons, or are present therein only in small amounts. As the tumour grows, an increase in the serum concentration of the marker may occur. The assessment of "medium" serum concentrations, however, is problematic in respect of establishing a diagnosis since that finding can both point to a normal value which although being anomalous is nevertheless harmless (e.g. genetically caused), as well as to the beginning of tumour growth. The decisive question is therefore whether there has been an increase in the serum concentration of such a tumour marker at a certain time. This question can be answered if the serum concentration of that tumour marker is examined at certain time intervals. Only in this way is it possible to recognize a beginning tumour growth at an early point and with relative certainty. In principle, such marker detections must be carried out for each test person at intervals of time (i.e. a sequential determination), so that a trend analysis can be performed.

The trend analyses or sequential determinations of tumour markers using the biochips of the present invention may also be utilized for development control or follow-up of tumours, e.g. for postoperative relapse control or for the control of a cytostatic therapy.

With the known archiving methods for patient samples the test series mentioned cannot be realised, or only at great cost. By contrast, with the biochips according to the present invention and the method according to the present invention it is now made possible to store this sample material in large numbers and in a space-saving manner for prolonged periods, and to perform a plurality of diagnostic detection reactions, e.g. for determination of tumour markers. This makes retrospective trend analyses possible which considerably accelerate the establishment of diagnoses. Because of the archivability of the biochips according to the invention it is now also possible in cases where new tumour markers are becoming known to test older biochips of a certain proband for the presence or absence of such tumour markers. The invention can thus contribute to recognizing tumour growth at an early stage and contribute to early appropriate intervention.

Furthermore, the biochips of the present invention are suitable for clinical research, where archiving patient sample material likewise plays a big part. This is of significance especially where—for instance when the formulation of the scientific problem is changed—later ascertainment becomes necessary on earlier patient samples. Compared to the currently utilized methods—freezing of samples (as a rule at least 0.5 ml) and later defrosting—the biochips according to the present invention are much more suitable since they enable a considerably larger number of detection reactions while at the same time requiring considerably less space and affording facilitated storage. Because of the large number of detection reactions made possible by one biochip there is also no longer any necessity of preparing and storing several parallel samples of a patient at a particular point in time.

A further application field of the biochips according to this invention are blood banks or firms or other organisations which process human donor material (e.g. body fluids, cells, tissues) and where samples of the donor material and possibly of products made therefrom must or should be stored for diagnostic detection reactions for purposes of control. Usually only the analysis results but not the samples themselves are stored as this would require too much space. However, in connection with occurring contaminations, it may also be advantageous to subject such samples again to an analysis, possibly using other detection methods, for example for legal safeguarding. A renewed analysis of such samples may also be of advantage if it is to be proved that a raw, intermediate or end product of human material in terms of its composition complied with the regulations or the provisions of the law. The biochips according to the invention may advantageously be used for archiving and subsequent analysis of samples of donor blood or other donor material from blood banks, companies and other organisations. If a contamination has occurred or there is a suspicion of non-conformity, the archived biochips make it possible to subsequently analyse the suspicious donor samples or samples of products based thereon. In this way it is possible to subsequently provide proof that a donor sample or product sample conformed to regulations, standards, or provisions of the law. This can be of great significance and assistance in particular in legal disputes. Furthermore, the inventive biochips or sample carriers may be used for storing and archiving patient sample material for purposes of routine diagnostic of patient samples.

The biochips according to this invention can also be advantageously utilised in epidemiological studies, to examine the proliferation of infectious diseases, for example. Hitherto such examinations frequently failed because the sample material from the past was no longer available since, for practical reasons, it was not possible to store the required numbers of blood samples or the like. In contrast thereto, the biochips described here enable a space-saving and economical long-term storage and archiving. It is thereby possible to archive a large number of samples. These samples are then available for later epidemiological studies; hence these studies are able to take into account a much larger patient collective as they can fall back on archived samples from the past.

The biochips and the methods according to the present invention can be utilised to advantage in connection with different formulations of problems in the field of medicine or veterinary medicine. Apart from the already mentioned application examples, applications for purposes of tissue typing or in the field of forensic medicine are also possible.

What is claimed is:

1. A diagnostic detection method for detecting the presence or absence of analytes in a biological sample material, comprising the steps of:
    a) making a biochip by binding said biological sample material which is obtained from body fluids or cells or tissue samples from an organism to be examined to a surface of a sample carrier, which surface is subdivided into micro-areas, by coating with a liquid or suspended sample material of said biological sample material, and subsequently drying, whereby said analytes which are present in the biological sample material are bound to said surface in a manner that does not specifically select a molecule;
    b) selecting at least one specific, diagnostic detection reagent that is known to specifically interact with or bind to said analyte;
    c) applying said at least one specific, diagnostic detection reagent to single micro-areas of the biochip, using a pipetting robot, and incubating under conditions suitable for the relevant detection reaction by which said reagent interacts with or binds to said analyte;
    d) applying wash liquids to suppress unspecific reactions, and subsequently drawing-off of these wash liquids;
    e) detecting measurement signals from positively reacting micro-areas;
    evaluating the signals for the presence or absence of the analytes and storing the measurement data.

2. The method according to claim 1, wherein the liquid or suspended sample material, prior to its binding to the surface of the sample carrier, is prepared by centrifugation, cell disintegration or extraction of the biological sample material.

3. The method according to claim 1, wherein each single specimen of the biochip has bound to its surface liquid or suspended sample material derived from an individual biological organism or from an individual patient.

4. The method according to claim 1, wherein said sample material is selected from body liquids, tissue samples, organ samples, or components, cells, fractions, concentrates or extracts obtained from said fluids, tissue samples or organ samples.

5. The method according to claim 4, wherein said body liquids comprise whole blood, plasma, serum, urine, ascites, amniotic water, saliva, liquor, lavage material from body cavities or bronchoalveolar lavage.

6. The method according to claim 1, wherein the surface of the sample carrier is coated with a linker layer by means of which the sample material is bound.

7. The method according to claim 6, wherein the linker layer comprises linker molecules which enable the selective binding or concentration of specific kinds of biological macromolecules selected from the group consisting of proteins, peptides, sugars, lipids, nucleic acids and cells.

8. The method according to claim 7, wherein said linker layer is present only in the region of each micro-area, the adjacent regions being free of said linker molecules.

9. The method according to claim 1, wherein the sample carrier has at least 100 micro-areas per $cm^2$, and the micro-areas are configured as depressions or are separated from each other by hydrophobic or non-wettable border areas.

10. The method according to claim 1, wherein steps b) to f) are performed on more than one biochip parallelly or simultaneously.

11. The method according to claim 1, wherein the individual micro-areas of a biochip are simultaneously treated with different specific diagnostic detection reagents.

12. The method according to claim 1, wherein the specific diagnostic detection reagents utilized in step b) are selected from the group consisting of antibodies, antigens, lectins, DNA-probes, biomolecule-binding dyes or other specifically binding molecules.

13. The method according to claim 1, wherein the detection of measurement signals takes place utilizing CCD-cameras, phototransistors, or radioactivity, fluorescence or luminescence detectors.

14. The method according to claim 1, wherein the same biochip which is coated with the sample material is subjected to an analysis according to steps b) to e) or b) to f), either twice or several times in succession, with the biochip being stored during the period between the successive analyses, and with different micro-areas of the biochip being treated with detection reagents in the successive analyses.

15. The method according to claim 1, wherein said biochip is provided with a machine-readable storage medium, and said method further comprises a step of storing said measurement data, or said evaluation of the data, on the machine-readable storage medium.

16. The method according to claim 15, wherein said machine-readable storage medium is a machine-readable magnetic strip or a digital storage element.

17. The method according to claim 1, wherein said biochip is provided with a machine-readable storage medium, and said method further comprises a step of storing patient-related data on the machine-readable storage medium.

18. The method according to claim 17, wherein said machine-readable storage medium is a machine-readable barcode, a machine-readable magnetic strip or a digital storage element.

19. The method according to claim 1, wherein said biochip is provided with a machine-readable storage medium, and said method further comprises the steps of:
registering the positions of the micro-areas which have already been used for a detection reaction; and
storing said positions on the storage medium of the biochip.

20. The method according to claim 1, wherein, in step b), different micro-areas of the same biochip are analyzed by applying the same detection reagent at different concentrations.

21. The method according to claim 1, wherein said at least one diagnostic detection reagent comprises a reagent capable of detecting the presence of a tumour marker present in the biological sample material.

22. The method according to claim 1, wherein the individual micro-areas of a biochip are sequentially treated with different specific diagnostic detection reagents.

23. The method according to claim 1, wherein the micro-areas are configured as depressions.

24. The method according to claim 1, wherein the micro-areas are separated from each other by hydrophobic or non-wettable border areas, said hydrophobic or non-wettable border areas preventing the binding of sample material.

25. The method according to claim 1, wherein the surface of the sample carrier used in step a) is pre-treated by etching or roughening to improve the binding capacity of the surface for the biological sample material.

26. The method according to claim 1, wherein in step a) the biological sample material is bound to the surface of the sample carrier only in the region of the micro-areas, the adjacent regions of the sample carrier being free of sample material.

27. The method according to claim 1, wherein the micro-areas are configured as depressions, the bottom of which is coated with a linker layer by means of which the sample material is bound to the matrix of the sample carrier.

28. The method according to claim 1, wherein said sample carrier comprises different area portions that differ from each other in that they are coated with different types of linker molecules.

29. The method according to claim 1, wherein said micro-areas are produced by employing a physical method selected from the group consisting of engraving, punching, embossing and printing.

30. The method according to claim 1, wherein said liquid or suspended sample material comprises whole blood, plasma, serum, urine, ascites, amniotic water, saliva, liquor, lavage material from body cavities or bronchoalveolar lavage.

* * * * *